United States Patent [19]
Hofmann et al.

[11] Patent Number: 5,676,646
[45] Date of Patent: Oct. 14, 1997

[54] FLOW THROUGH ELECTROPORATION APPARATUS

[75] Inventors: Gunter A. Hofmann; Henry R. Kent, both of San Diego, Calif.

[73] Assignee: Genetronics, Inc., San Diego, Calif.

[21] Appl. No.: 615,090

[22] Filed: Mar. 14, 1996

Related U.S. Application Data

[60] Division of Ser. No. 320,966, Oct. 12, 1994, Pat. No. 5,545,130, which is a continuation-in-part of Ser. No. 865,347, Apr. 8, 1992, abandoned.

[51] Int. Cl.$^6$ .................................................. A61M 37/00
[52] U.S. Cl. ............................................. 604/4; 604/20
[58] Field of Search ........................... 604/20–21, 4–6; 435/173.6; 935/52

[56] References Cited

U.S. PATENT DOCUMENTS

| | | |
|---|---|---|
| 4,464,166 | 8/1984 | Edelson . |
| 4,496,443 | 1/1985 | Mack et al. . |
| 4,612,007 | 9/1986 | Edelson . |
| 4,849,089 | 7/1989 | Marshall, III . |
| 5,098,843 | 3/1992 | Calvin . |
| 5,501,662 | 3/1996 | Hofmann . |

FOREIGN PATENT DOCUMENTS

| | | |
|---|---|---|
| 0 324 153 A3 | 12/1988 | European Pat. Off. . |
| WO 94/21117 | 9/1994 | WIPO . |
| WO 96/12006 | 4/1996 | WIPO . |

*Primary Examiner*—Mark Bockelman
*Attorney, Agent, or Firm*—Baker, Maxham, Jester & Meador

[57] ABSTRACT

A flow through apparatus for implanting molecules into living blood cells of a patient, comprises a housing including an elongated flow through chamber having an inlet and an outlet at opposite ends thereof, a pair of elongated spaced apart parallel electrodes disposed between the inlet and the outlet for fluid to flow therebetween, a continuous flow shunt including a pump for withdrawing blood from a patient, passing it through the flow through chamber between the electrodes and returning it to the patient, apparatus for injecting a predetermined quantity of fluid medium carrying preselected molecules into the blood after it has been drawn from the patient and before it passes through said chamber, and an electrical source for applying a predetermined electric signal of a predetermined amplitude and duration to the electrodes for generating and repeatedly applying electric fields of a predetermined amplitude and duration to the flow of the mixture of blood and fluid medium in order to make the walls of preselected cells in the blood transiently permeable to permit molecules to enter the preselected cells without killing the cells.

20 Claims, 5 Drawing Sheets

FLOW THROUGH ELECTROPORATION APPARATUS

This application is a division of application Ser. No. 08/320,966, filed Oct. 12, 1994, now U.S. Pat. No. 5,545,130 which is a continuation-in-part of my application Ser. No. 07/865,347 filed Apr. 8, 1992, now abandoned, entitled ELECTROPORATION MEDIATED, EX VIVO, INTRA CELLULAR DRUG AND GENE DELIVERY METHOD AND APPARATUS.

BACKGROUND OF THE INVENTION

The present invention relates to the treatment of ailments in humans and other mammals, and more particularly, to an apparatus and method for continuous flow delivering pharmaceutical compounds and genes into live cells of a patient.

It has long been known that it would be desirable to target certain cells within the body with specific pharmaceutical compounds. For example, in the treatment of certain types of cancer with chemotherapy it is necessary to use a high enough dose of a drug to kill the cancer cells without killing an unacceptably high number of normal cells. If the chemotherapy drug could be inserted directly inside the cancer cells, this objective could be achieved. However, some of the best anti-cancer drugs, for example, bleomycin, normally cannot penetrate the membranes of certain cancer cells.

Similarly, certain diseases could be treated by introducing desired genes into the specific cells of the patient. At present, most gene therapy experiments have utilized retroviruses as the carrier of the gene into the cells. When a retrovirus enters a target cell, it integrates essentially randomly in the genome and thus has the potential for introducing mutational damage by the mere fact of its insertion. If the virus integrates adjacent to an oncogeny, malignant transformation of the target cell can result. Many of these drawbacks can be alleviated by using electroporation for gene transfer.

It is known that genes and other molecules and macromolecules such as pharmaceutical compounds can be incorporated into live cells through a process known as electroporation. The genes or other molecules and macromolecules are mixed with the live cells in a buffer medium and short pulses of high electric fields are applied. The high electric field pulses cause the cell membranes to become transiently porous and the genes or macromolecules enter the cells. There they can modify the genome of the cell. There is good evidence that electroporated genes can recombine with their homologous host gene. Examples of the prior art are: U.S. Pat. No. 4,970,154 of Chang, U.S. Pat. No. 5,098,843 of Calvin and U.S. Pat. No. 5,128,257 of Baer.

The incorporation of drugs into red blood cells via electroporation as well as the incorporation of genes into white blood cells via electroporation have both been demonstrated. The selective incorporation of genes into white blood cells in whole blood via electroporation has also been demonstrated. The electroporation of cells in a flow through system utilizing a venturi in a static field has been proposed by Calvin in U.S. Pat. No. 5,098,843.

Heretofore, an apparatus and method have not been provided to permit electroporation mediated, ex vivo, intra cellular drug and gene delivery through the blood vessels of a living patient. It would be desirable to provide such an apparatus and method because it would permit gene therapy of living patients by genetically modifying their lymphocytes. Such an apparatus and method would also be beneficial in providing a means for delivering drugs to selected tissues and organs of a living human body by encapsulating them into red blood cells. In general, such an apparatus and method would be advantageous in providing a means of delivery of antibodies, proteins, or other macromolecules into the red or white blood cells of a living patient.

SUMMARY OF THE INVENTION

Accordingly, it is the primary object of the present invention to provide an improved flow through electroporation apparatus.

It is another principal object of the present invention to provide an apparatus for electroporation mediated, ex vivo, intra cellular drug and gene delivery. It is a further object of the present invention to provide a method of electroporation mediated, ex vivo, intra cellular drug and gene delivery for a living patient.

My invention provides a useful apparatus and method for implanting macromolecules such as genes and pharmaceutical compounds into living blood cells of a patient. The apparatus includes an improved housing structure having a disposable chamber with an elongated electroporation section. A pair of catheters are implanted into the patient for drawing out and returning the patient's blood. Once the blood is drawn out utilizing a peristaltic pump a predetermined quantity of a fluid medium carrying preselected macromolecules is injected into the blood. Thereafter, electric fields are repeatedly applied to the mixture of blood and fluid medium in a flow through chamber having a pair of elongated spaced apart parallel electrodes. These fields have a predetermined amplitude and duration that makes the walls of the preselected cells transiently permeable to permit the macromolecules to enter said preselected cells without killing them. Thereafter the mixture of blood and fluid medium is infused back into the patient. The electric fields are generated by applying a predetermining electric signal to the electrodes utilizing a signal generator.

A flow through apparatus for implanting molecules into living blood cells of a patient, comprises housing means including an elongated flow through chamber having an inlet and an outlet at opposite ends thereof, and a pair of elongated spaced apart parallel electrodes disposed between the inlet and the outlet for fluid to flow between, continuous flow shunt means for withdrawing blood from a patient, passing it through said flow through chamber between said electrodes and returning it to the patient, means for injecting a predetermined quantity of fluid medium carrying preselected molecules into the blood after it has been drawn from the patient and before it passes through said chamber, and means for applying a predetermined electric signal of a predetermined amplitude and duration to said electrodes for generating and repeatedly applying electric fields of a predetermined amplitude and duration to the flow of the mixture of blood and fluid medium in order to make the walls of preselected cells in the blood transiently permeable to permit molecules to enter said preselected cells without killing said cells.

BRIEF DESCRIPTION OF THE PREFERRED EMBODIMENTS

Figure 1:
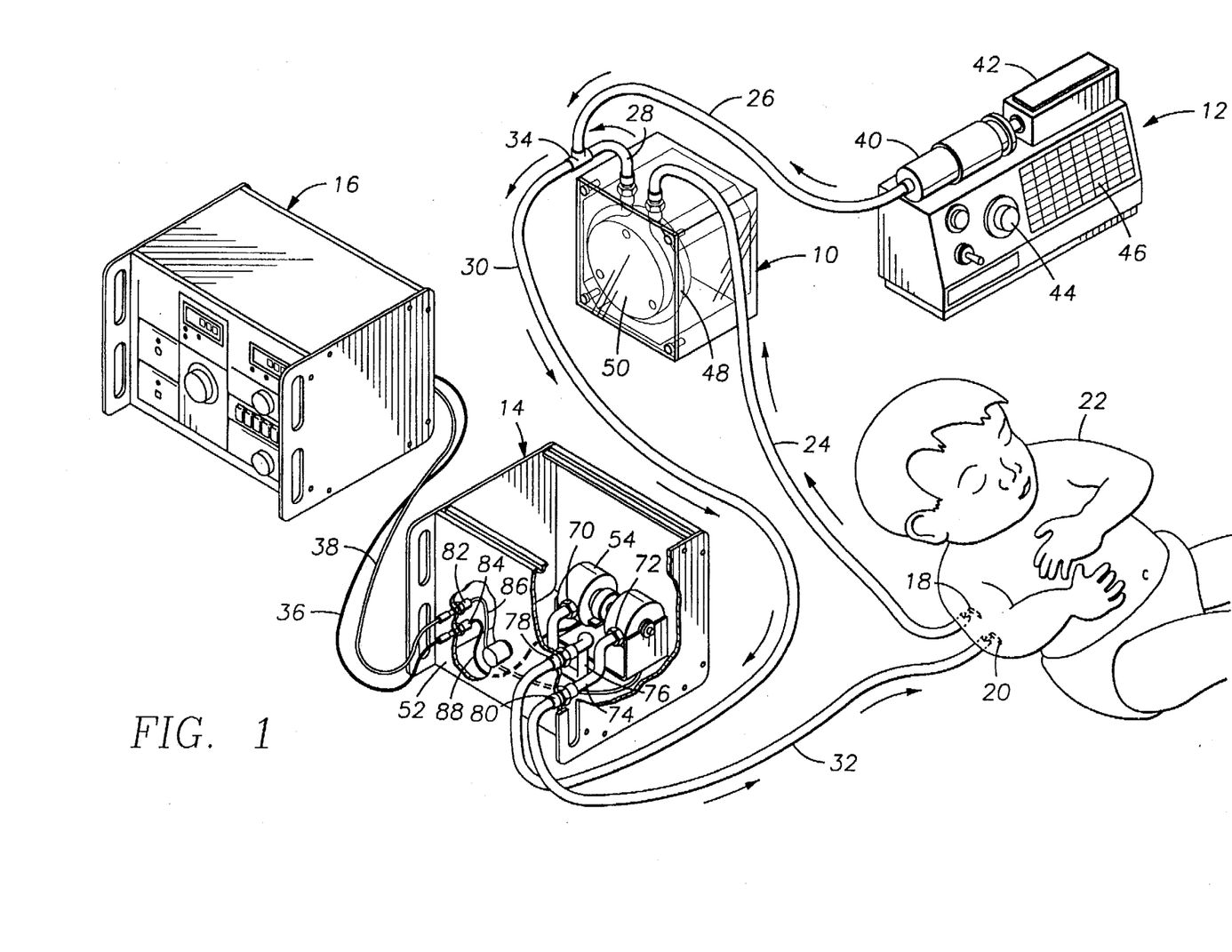
FIG. 1 illustrates a preferred embodiment of an apparatus for electroporation mediated, ex vivo, intra cellular drug and gene delivery.

Referring to FIG. 1, the preferred embodiment of my apparatus comprises a peristaltic pump 10, and injection pump 12, a flow through chamber unit 14 and a signal generator 16. The apparatus further comprises shunt means in the form of a pair of implantable catheters illustrated diagrammatically at 18 and 20 for drawing out and returning blood from veins in the arm of a patient 22. The apparatus further comprises segments 24, 26, 28, 30 and 32 of suitable IV tubing along with a T-shaped coupling 34 for enabling fluid flow between the pumps, flow through chamber unit and catheters in the directions indicated by the dark arrows in FIG. 1. Finally, the apparatus includes a pair of electric cables 36 and 38 for connecting the signal generator 16 and the flow through chamber unit 14.

The injection pump 12 may be of the conventional type that employs a syringe 40 for holding a quantity of a fluid medium carrying preselected macromolecules such as genes or pharmaceutical compounds. The plunger of the syringe 40 is pushed inwardly (to the left in FIG. 1) by a motor driven piston assembly 42. The rate of delivery of the fluid medium from the syringe 40 through the IV tubing segment 26 may be manually adjusted via control dial 44 with the delivery parameters being indicated on a display 46.

The peristaltic pump 10 is of conventional design and has controls (not illustrated) for adjusting the rate of pumping. The peristaltic pump actively pumps the blood outside the patient 22 in a circulatory fashion. It includes a replaceable tubing segment 48 which surrounds a cylindrical housing 50. A motor driven rotor (not visible) engages the tubing segment 48 to propel the blood therethrough to T-shaped coupling 34 where it mixes with the fluid medium from he injection pump 12. This fluid medium may be a pharmaceutical compound suspended in a suitable liquid vehicle such as saline solution. Where genes are to be introduced into the blood cells of the patient, the fluid medium comprises the genes suspended in a suitable liquid medium that will support the viability of the genes until they are inserted into the blood cells of the patient. Such fluid medium are well known to those skilled in the art.

Figure 2:
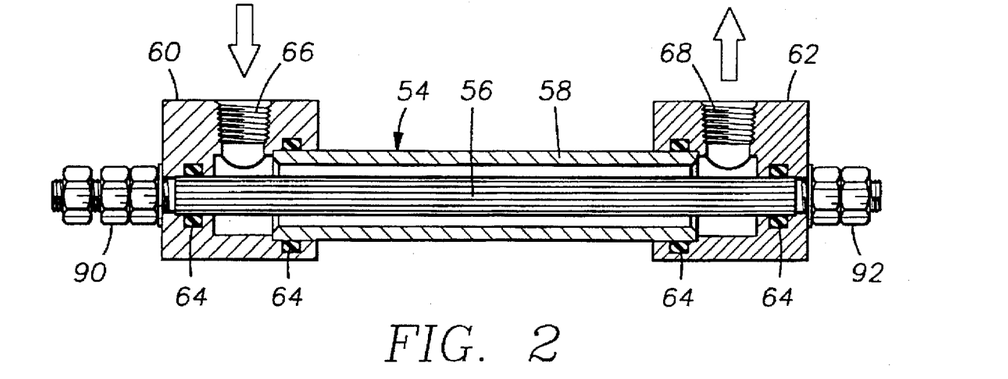
FIG. 2 is a sectional view through a coaxial flow through chamber that is utilized in an exemplary embodiment of the invention illustrated in FIG. 1.

The flow through chamber unit 14 comprises a rectangular outer housing 52 which encloses an elongated flow through chamber 54. Details of the flow through chamber 54 are illustrated in FIG. 2. It includes a pair of uniformly spaced apart elongated electrodes in the form of a cylindrical conductive rod 56 concentrically mounted with a cylindrical vessel 58 defining opposed parallel electrode surfaces. Preferably, the rod 56 and vessel 58 are made of stainless steel and may be gold plated where desired. The ends of the rod 56 and vessel 58 are mounted in hollow blocks 60 and 62 of insulating, plastic material and sealed with high temperature elasticomeric O-rings 64. The O-rings are seated within circular groves machines inside the blocks 60 and 62. They are preferably made of a high temperature resistant material such as that sold under the trademark VITON so that the entire flow through chamber can be sterilized in an autoclave.

The blocks 60 and 62 have cylindrical holes bored therein for receiving the ends of the rod 56 and vessel 58. The blocks 60 and 62 have inlet and outlet ports, 66 and 68, respectively formed therein so that the mixture of blood and fluid medium can pass through the flow through chamber between the opposed electrodes as indicated by the arrows in FIG. 2. Fittings 70 and 72 (FIG. 1) are screwed into the threaded walls of the inlet and outlet ports at 66 and 68 for coupling tubing segments 74 and 76 thereto. The tubing segments 74 and 76 extend within the housing 52 and are in mm connected to fitting 78 and 80 mounted on the front panel of the housing. The tubing segments 30 and 32 are connected to the fittings 78 and 80, respectively.

The electric cables 36 and 38 (FIG. 1) from the signal generator 16 have plugs that are removably connected to jacks 82 and 84 on the front panel of the housing 52 of the flow through chamber unit. These jacks are in turn connected to wires 86 and 88 which connect to threaded shaft and nut assemblies 90 or 92 (FIG. 2) as one electrode and to a clamp around vessel 58 as the other electrode of the flow through chamber 54. The assembly 90 provides an electrical connection to the rod electrode 56 while the assembly 92 provides an electrical connection to the vessel electrode 58.

Details of the signal generator 16 (FIG. 1) will now be described. The function of the signal generator is to generate a predetermined electric signal which, when applied to the electrodes 56 and 58 of the flow through chamber 54, results in applying electric fields of a predetermined amplitude and duration to the mixture of blood and fluid medium flowing therethrough. Preferably these fields are applied repeatedly and their amplitude and duration make the walls of preselected cells in the blood sufficiently permeable to permit the macromolecules to enter the preselected cells without killing them.

One suitable signal generator is the ELECTRO CELL MANIPULATOR Model ECM 600R commercially available from Genetronics, Inc. of San Diego, Calif., U.S.A. The ECM 600 signal generator generates a pulse from the complete discharge of a capacitor which results in an exponentially decaying waveform. The electric signal generated by the ECM 600R, signal generator is characterized by a fast rise time and an exponential tail.

A number of variables are considered in achieving a desired pulse length with the ECM 600R signal generator. These include the buffer type, voltage and timing mode, fill volume, and chamber type used. The chamber resistance is determined by the type of medium. It can also be altered by changing the volume in the chamber, i.e., a smaller volume equates to a higher resistance. A change in the volume in the chamber changes the resistance and pulse length in an inverse relationship. If the total chamber resistance is much greater than the timing resistor remains active and gives the desired pulse length. If the chamber resistance is lower than the timing resistor chosen, then the pulse length is determined by the chamber resistance. The chamber resistance essentially determines the longest pulse length that can be achieved. In the ECM 600R signal generator, the electroporation pulse length is set by selecting one often timing resistors marked R1 through R10. They are active in both High VM (capacitance fixed at fifty microfarads) and Low VM (with a capacitance range from 25 to 3,175 microfarads).

The passage of an electrical current across the cell membrane results in the creation of transient pores which are critical to the electroporation process. The ECM 600R signal generator provides the voltage (in kV) that travels across the chamber gap (in cm) between the electrodes. This potential difference defines what is called the electric field strength where E equals kV/cm. Each cell species has its own critical field strength for optimum electroporation. This is due to cell size, membrane make-up and individual characteristics of the cell wall itself. For example, some Gram positive bacteria are quite resistant to electroporation and require very high field strengths, i.e., greater than 17 kV (cm), before cell death and/or electroporation occurs. Generally, the required field strength varies inversely to the size of the cell.

The ECM 600R signal generator has a knob that permits the adjustment of the amplitude of the set charging voltage applied to the internal capacitors from 50 to 500 volts in Low VM and from 0.05 to 2.5 kV in the High VM. The amplitude of the electrical signal is shown on a display incorporated into the ECM 600R signal generator. This device further includes a plurality of push button switches for controlling pulse length, in the LOW VM mode, by a simultaneous combination of resistors parallel to the output and a bank of seven selectable additive capacitors.

The ECM 600R signal generator also includes a single automatic charge and pulse push button. This button may be depressed to initiate both charging of the internal capacitors to set the voltage and to deliver a pulse to the flow through chamber in an automatic cycle that takes less than five seconds. The manual button may be sequentially pressed to repeatedly apply the predetermined electric field to the mixture of blood and fluid medium or a repetitive charge/pulse mode may be selected with an adjustable repetition rate.

The waveforms of the electrical signal provided by the signal generator 16 can be an exponentially decaying pulse, a square pulse, a unipolar oscillating pulse train or a bipolar oscillating pulse train. The electric field strength can be 0.2 kV cm to 20 kV/cm. The pulse length can be ten microseconds to one hundred milliseconds. There can be one to one hundred pulses per liquid volume element as it passes through the flow chamber. Of course the waveform, electric field strength and pulse duration are dependent upon the type of cells and the type of macromolecules that are to enter the cells via electroporation.

Figure 3:
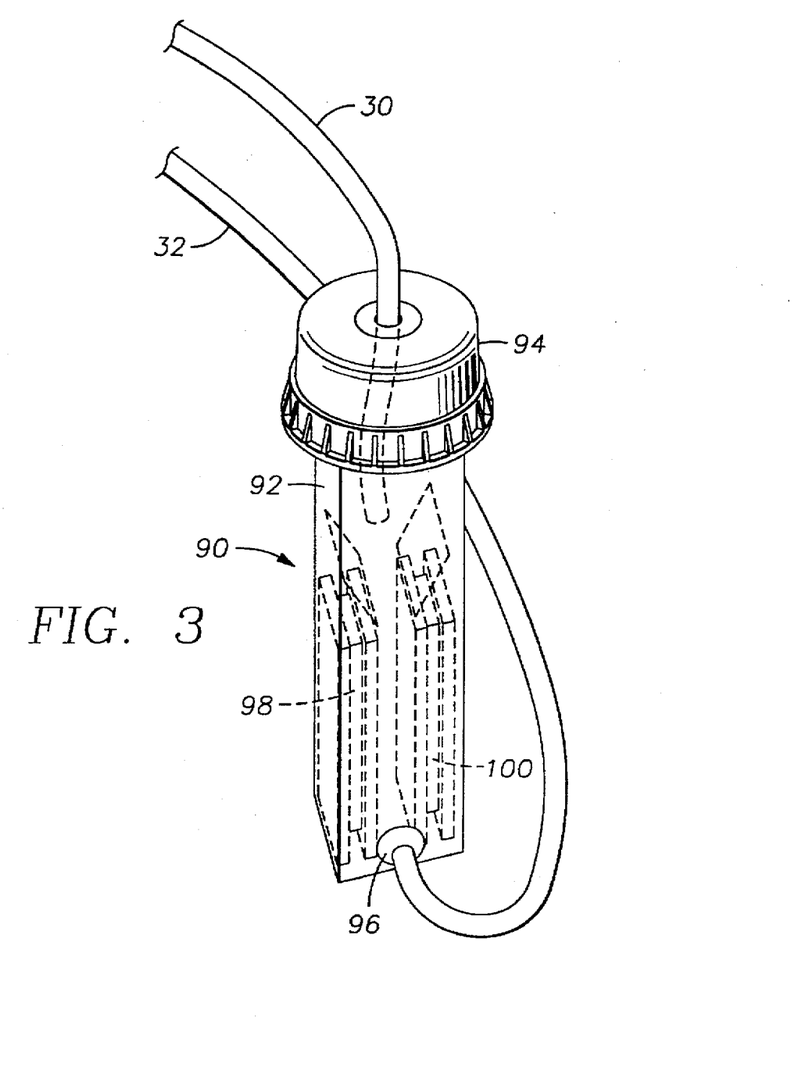
FIG. 3 is an elevation view of a cuvette-type flow through chamber that may be utilized in the embodiment illustrated in FIG. 1.

FIG. 3 illustrates an alternate flow through chamber in the form of a disposable cuvette chamber 90. The cuvette chamber comprises a clear plastic rectangular housing defining an enclosure 92 having a round opening at the upper end. This opening is closed by a push-on plastic cap 94. The tubing segment 30 extends snugly through a hole in the middle of the cap 94 at one end of the chamber. The tubing segment 32 extends through a hole in the lower end of the enclosure 92 which is sealed with a fitting 96. The enclosure 92 is preferably molded with a pair of embedded elongated electrodes 98 and 100 which are connected to cables 36 and 38 that carry the electrical signal from the signal generator 16 within a safety stand (not shown) having spring contacts. The electrodes are uniformly spaced apart and extend parallel, substantially the full length of the chamber, between the inlet and outlet to enable fluid to pass therebetween. The electrodes may be of any suitable conductive material such as stainless steel or aluminum and may be gold plated where desired. Preferably, the disposable cuvette chamber 90 is gamma irradiated for guaranteed sterility.

A typical protocol for the electroporation of blood lymphocytes is set forth hereafter:

Primary Human Peripheral Blood Lymphocytes CCFR-CEM T-Lymphoblastoid cells
Plasmid:pBL3CMV
Cell Preparation:

| | |
|---|---|
| Growth Medium: | RPMI 1640 with 10% fetal calf serum |
| Harvest Phase: | Logarithmic Growth |
| Washing Procedure: | Pellet by centrifugation |
| Wash 1: | Resuspend with PBS |
| Final Cell Density: | $2 \times 10^7$ viable cells/ml |
| Electroporation Settings: | |
| Choose Mode: | T 500 V/CAPACITANCE & RESISTANCE (LV) |
| Set Capacitance: | C 2700–3000 uf |
| Set Resistance | BTX Disposable Cuvette P/N 620 (2 mm gap) |
| Set Charging Voltage | S 110 V |
| Desired Field Strength: | 0.55 kV/cm |
| Desired Pulse Length: | t 50–55 msec |
| Electroporation Procedure: | Pre chill Cuvettes |
| Cell Volume: | 18 ul |
| Cell Density: | $2 \times 10^7$ cell/ml |
| Transfectant: | 50 ug plasmid DNA (supercoiled) in 20 ul PBS |
| Total Reaction Volume: | 200 ul |
| Operating Temperature: | Hold mixture at Room Temperature for 10 min Press A to activate Automatic Charge and Pulse sequence |
| Dilution Media: | 6 ml RPMI 1640 with 10% fetal calf serum |
| Post Pulse Incubation: | Hold at 37° C. in 5% $CO_2$ for 24–48 hrs |
| Selection Method: | CAT assay |

Figure 4:
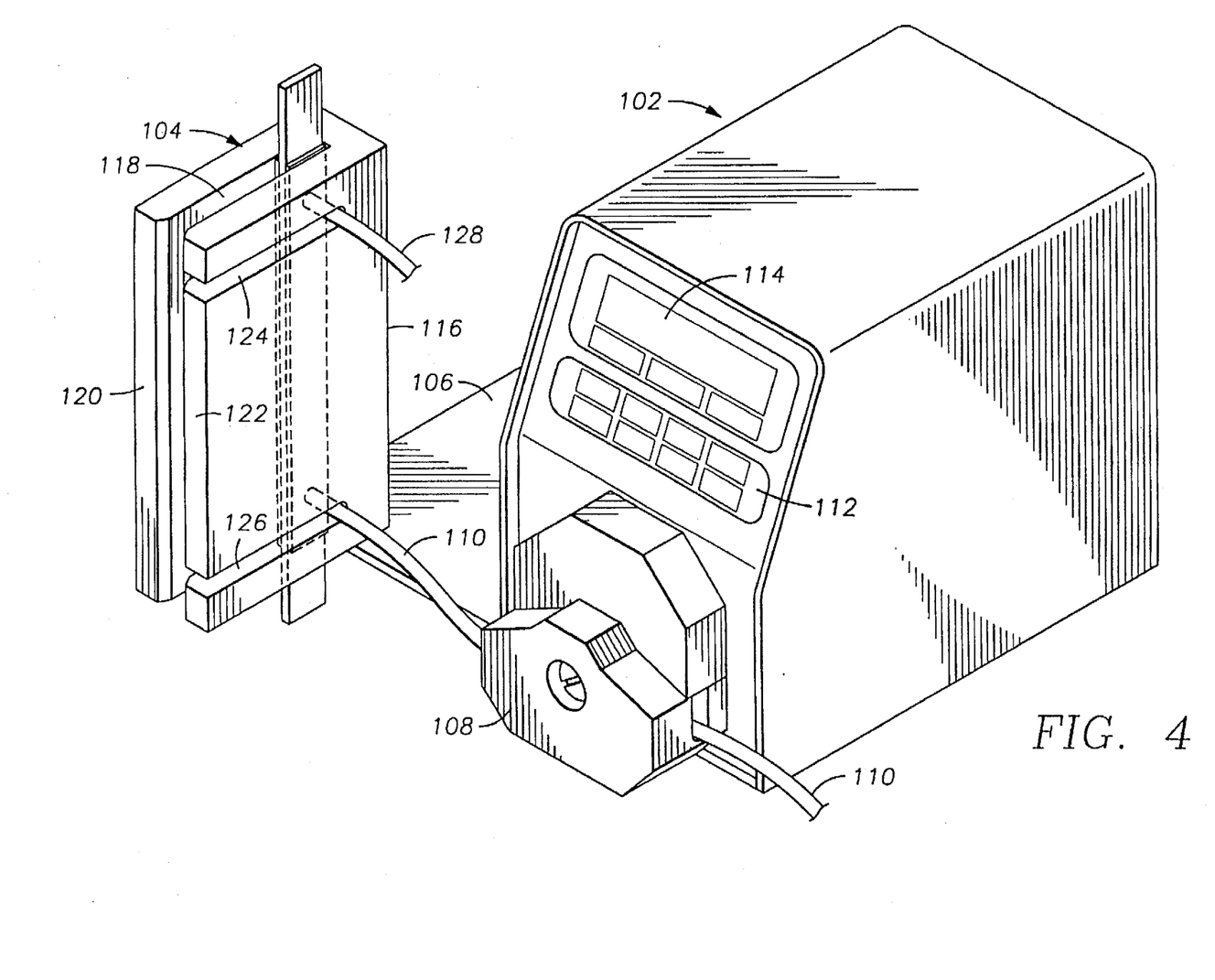
FIG. 4 is a perspective view of an alternate embodiment of pump and chamber components of the system.

Referring to FIG. 4 of the drawing an alternative embodiment of a combination peristaltic pump 102 and flow through chamber assembly 104 is illustrated and is mounted on a common support platform 106 for convenience of assembly and use. The peristaltic pump has a rotor assembly 108 for receiving tubing 110. A control panel 112 provides means for selection and control of various parameters of the pump unit, including start-stop directional pumping and rate of pumping and time etc. The pump assembly is also provided with suitable digital readout panel 114 providing a visual readout of certain selected parameters or operating conditions.

The flow through electroporation chamber assembly includes a safety stand 116, having a generally U-configuration with a slot 118 for receiving the disposable chamber formed between opposing sides, or panels 120 and 122. The side panel 122 is provided with upper and lower slots 124 and 126, respectively, for receiving the fluid or tubes 110 and 128 connected to the chamber.

Figures 5, 9:
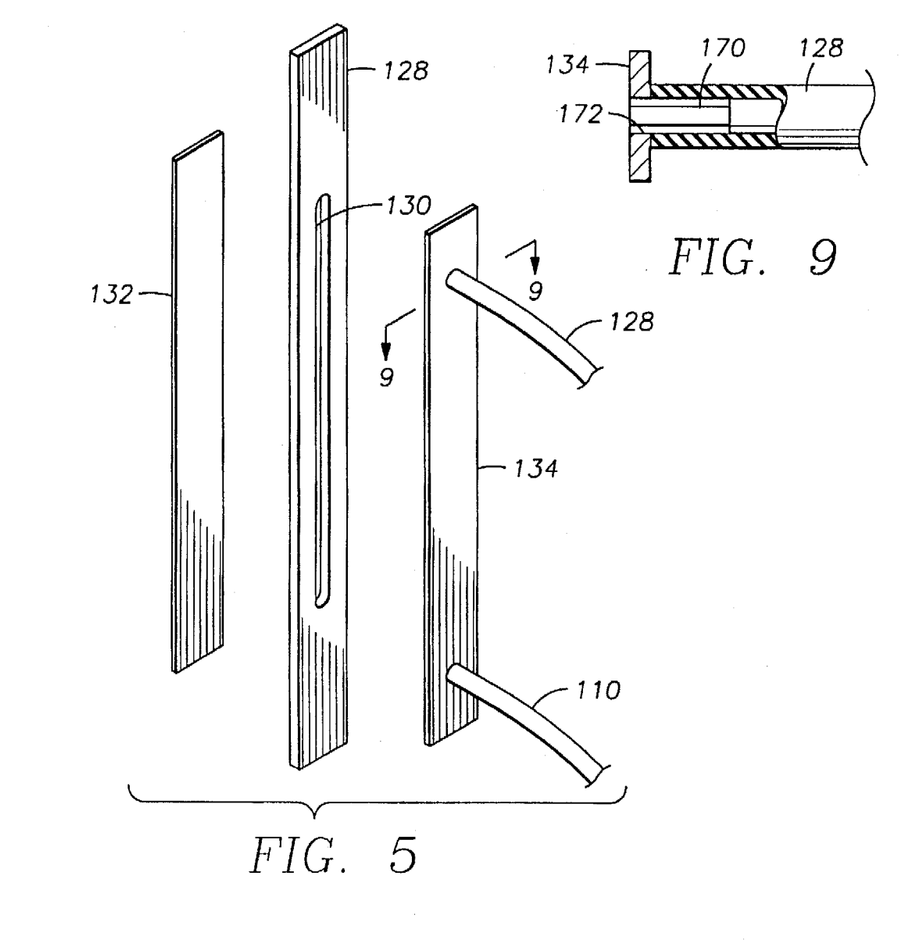
FIG. 5 is an exploded view illustrating details of the chamber of the embodiment of FIG. 4.
FIG. 9 is a section view taken on the line 9—9 of FIG. 5.

Referring to FIG. 5, details of the flow through chamber construction are illustrated. The chamber comprises a central generally rectangular barshaped body member 128 having an elongated centrally disposed through slot 130 formed therein. The slot 130 is enclosed on opposite sides of the barshaped body member 128 by means of a pair of bar shaped electrodes 132 and 134. The central body member 128 is preferably constructed of a non-conductive material whereas the bar electrodes 132 and 134 are preferably constructed of conductive material that can easily be gold-plated, at least along the surfaces, in communication with the sides of the slot. The electrode 134 is provided with upper and lower tube connections for attachment of the tubes 110 and 128 for opening communications directly with the upper and lower ends, respectively, the slot 130.

The flow through chamber is assembled with the electrodes 132 and 134, sealingly engaging opposite sides of the bar 128 enclosing the slot 130. The electrodes are preferably, sealingly bonded by suitable means to the opposite sides of the central bar member.

Figure 6:
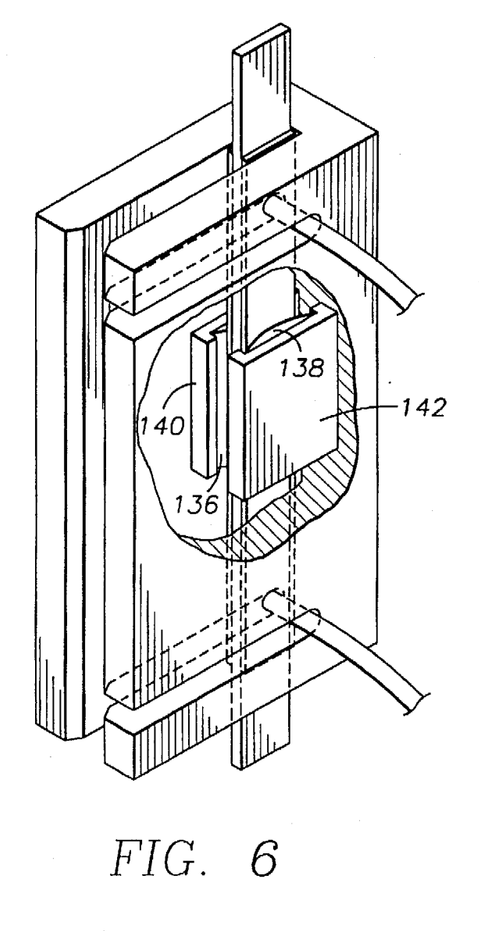
FIG. 6 is a perspective view with portions broken away illustrating the assembled chamber of FIG. 5 positioning in the chamber holder.

The assembled chamber then slides into the open slot 118 in the safety stand 116 between a pair of opposing spring contacts 136 and 138. These contacts are of a suitable conductive material, such as a copper alloy and are mounted in conductive holders 140 and 142, which are in turn attached to conductive cables. A pair of conductive cables, 144 and 146, include leads 148 and 150 connected such as by soldering to the respective holders 140 and 142.

Figure 7:
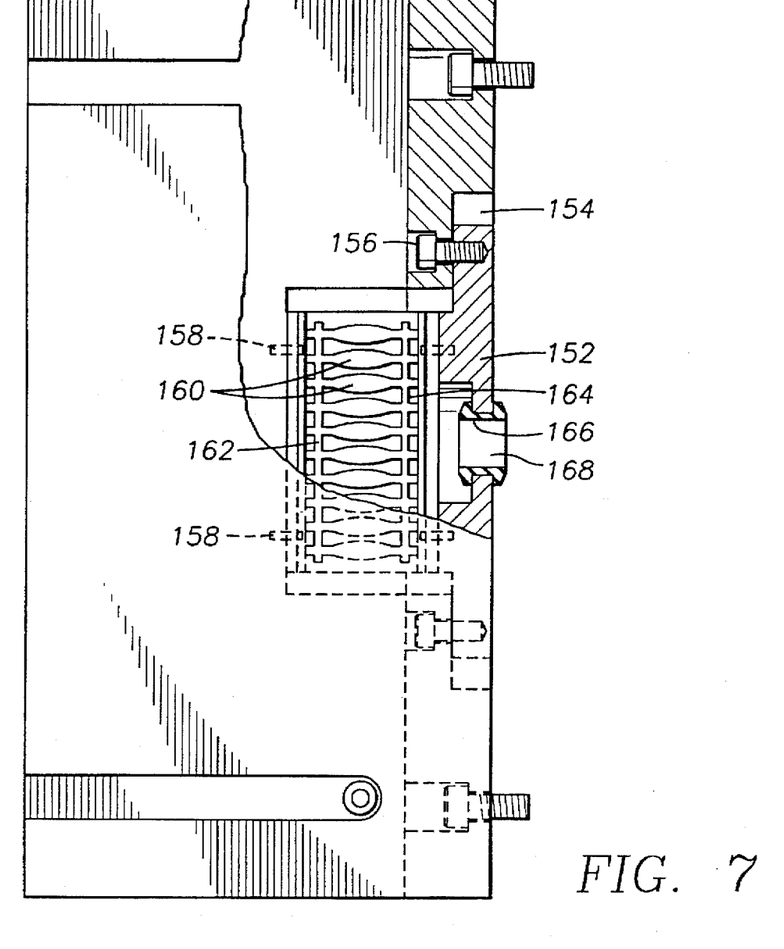
FIG. 7 is a side elevation view of the holder of FIG. 6 with portions broken away to reveal details of construction.
Figure 8:
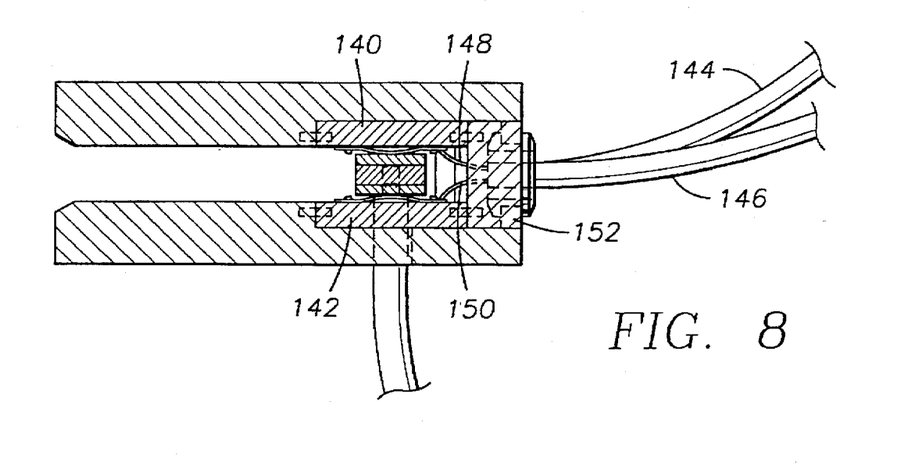
FIG. 8 is a top view of the embodiment of FIG. 7 with a portion sectioned to show details.

Referring to FIG. 7, the contact construction is best illustrated wherein the holders are mounted on a removable backplate 152, with an opening 154 in the back of the housing 116. The backplate is held in position such as by screws or the like 156. In the illustrated embodiment the holders 140 and 142 are mounted within the housing and to the backplate 152 by a plurality of pins 158.

Spring contacts 136 and 138 may have any suitable construction, but in a preferred form is constructed to have a somewhat louvered configuration, as illustrated in FIG. 7. As illustrated, the contact 136 is formed of a ladder-like construction, having a plurality of spaced outwardly bowed contact members 160, extending between a pair of laterally positioned parallel side members 162. This provides self-cleaning contacts that are biased into surface contact with the electrodes 132 and 134.

The cables 144 and 146 pass or extend through an opening 166 having a gromit 168 in the backplate 152.

Referring to FIG. 9, a section view taken on the line 99 of FIG. 5 illustrates the details of the connection of the tube or fluid line to the opening conduit through the electrode 134. A tube 170 extends through an opening 172 into the electrode and communicates directly with the upper end of the slot 130 and thus the chamber formed thereby. The fluid tube 128 is attached to the tube 170 in the usual manner by slipping over the tube and being clamped or otherwise attached thereto by suitable bonding.

While I have described preferred embodiments of my apparatus and method for electroporation mediated, ex vivo drug and gene delivery, it should be understood that modifications and adaptations thereof will occur to persons skilled in the art. Therefore, the protection afforded my invention should only be limited in accordance with the scope of the following claims.

We claim:

1. A flow through apparatus for implanting molecules into living blood cells of a patient, comprising:

housing means including an elongated flow through chamber having an inlet and an outlet at opposite ends thereof;

a pair of elongated spaced apart electrodes disposed in parallel relation over their entire lengths and extending along opposite sides of said chamber between the inlet and the outlet for fluid to flow between;

continuous flow shunt means for withdrawing blood from a patient, passing it through said flow through chamber between said electrodes and returning it to the patient;

means for injecting a predetermined quantity of fluid medium carrying preselected molecules into the blood after it has been drawn from the patient and before it passes through said chamber; and means for applying a predetermined electric signal of a predetermined amplitude and duration to said electrodes for generating and repeatedly applying electric fields of a predetermined amplitude and duration to the mixture of blood and fluid medium in order to make the walls of preselected cells in the blood transiently permeable to permit molecules to enter said preselected cells without killing said cells.

2. An apparatus according to claim 1 wherein said housing means comprises a generally elongated non-conductive bar member having a rectangular cross section and an elongated through slot intermediate the ends thereof;

said electrodes are elongated flat conductive members sealingly applied to opposite sides of said bar member closing said slot and defining said elongated flow through chamber.

3. An apparatus according to claim 2 wherein said inlet and said outlet are formed in one of said electrodes and communicate with opposite ends of said slot.

4. An apparatus according to claim 3 wherein said housing means comprises a generally U-shaped housing formed of a non-conducting material and having a pair of parallel side walls with an opening therebetween for removably receiving said flow through chamber; and spring biased electrical contacts in said side walls for engaging and electrically connecting to said electrodes.

5. An apparatus according to claim 4 wherein said U-shaped housing includes slots in one side thereof for accommodating tubing connected to said inlet and said outlet.

6. An apparatus according to claim 1 wherein said electrodes extend substantially the full length of the flow through chamber.

7. An apparatus according to claim 6 wherein said flow through chamber comprises an elongated non-conductive tubular member;

a header on one end of said tubular member defining one of said inlet and said outlet; and a pair of elongated conductive bars extending along opposite sides of said tubular member defining said electrodes.

8. An apparatus according to claim 1 wherein:

said flow through chamber comprises an elongated conductive tubular member defining one of said electrodes, and a pair of headers on the ends of said tubular member defining said inlet and said outlet; and a conductive rod extending coaxially of said tubular member defining the other of said conductors.

9. An apparatus according to claim 1 wherein said flow through chamber substantially rectangular in cross section.

10. An apparatus according to claim 9 wherein said flow through chamber comprises an elongated nonconductive tubular member;

a header on one end of said tubular member defining one said inlet and said outlet; and a pair of elongated conductive bars extending along opposite sides of said tubular member defining said electrodes.

11. A flow through apparatus for implanting molecules into living blood cells of a patient, comprising:

a housing having means defining an elongated flow through chamber having an inlet and an outlet;

a pair of elongated electrodes, said electrodes disposed in spaced apart parallel relation along their entire lengths and extending along said chamber between the inlet and the outlet, said electrodes being positioned for enabling fluid to flow between them;

continuous flow shunt means for withdrawing blood from a patient, passing it through said flow through chamber between said electrodes and returning it to the patient;

means for injecting a predetermined quantity of fluid medium carrying preselected molecules into the blood after it has been drawn from the patient and before it passes through said chamber; and electrical signal generating means for generating and applying a predetermined electric signal of a predetermined amplitude and duration to said electrodes for repeatedly generating and applying electric fields of a predetermined amplitude and duration to the mixture of blood and fluid medium in order for making the walls of preselected cells in the blood transiently permeable enable molecules to enter said preselected cells without killing said cells.

12. An apparatus according to claim 11 wherein said housing comprises a generally elongated non-conductive bar member having a rectangular cross section and an elongated through slot intermediate the ends thereof;

said electrodes are elongated flat conductive members sealingly mounted to opposite sides of said bar member closing said slot and defining said elongated flow through chamber.

13. An apparatus according to claim 12 wherein said inlet and said outlet extend through at least one of said electrodes and communicate with opposite ends of said slot.

14. An apparatus according to claim 13 wherein:

said housing comprises a generally U-shaped holder formed of a non-conducting material and having a pair of parallel side walls with an opening there between for removably receiving said flow through chamber; and spring biased electrical contacts disposed between said side walls for engaging and electrically connecting to said electrodes.

15. An apparatus according to claim 14 wherein said U-shaped holder includes slots in at least one side thereof for accommodating tubing connected to said inlet and said outlet.

16. An apparatus according to claim 11 wherein said electrodes extend substantially the full length of the flow through chamber.

17. An apparatus according to claim 16 wherein:

said flow through chamber comprises an elongated non-conductive tubular member;

a header at one end of said tubular member defining one of said inlet and said outlet; and a pair of elongated conductive bars extending along opposite sides of said tubular member defining said electrodes.

18. An apparatus according to claim 11 wherein:

said housing comprises an elongated conductive tubular member defining said chamber and one of said electrodes;

a pair of headers on the ends of said tubular member defining said inlet and said outlet; and a conductive rod extending coaxially of said tubular member defining the other of said electrodes.

19. An apparatus according to claim 11 wherein said flow through chamber substantially rectangular in cross section.

20. An apparatus according to claim 19 wherein:

said flow through chamber comprises an elongated non-conductive tubular member;

a header on one end of said tubular member defining one said inlet and said outlet; and a pair of elongated conductive bars extending along opposite sides of said tubular member defining said electrodes.

* * * * *